United States Patent [19]

Parodi et al.

[11] Patent Number: 5,219,355

[45] Date of Patent: Jun. 15, 1993

[54] BALLOON DEVICE FOR IMPLANTING AN AORTIC INTRALUMINAL PROSTHESIS FOR REPAIRING ANEURYSMS

[76] Inventors: Juan C. Parodi, Mercedes 4255, Buenos Aires, Argentina, 1419; Hector D. Barone, Maza 1869/73, Buenos Aires, Argentina, 1240

[21] Appl. No.: 769,964

[22] Filed: Oct. 2, 1991

[30] Foreign Application Priority Data

Oct. 3, 1990 [AR] Argentina ............................... 317999

[51] Int. Cl.⁵ ............................................ A61M 29/00
[52] U.S. Cl. .................................... 606/191; 606/194; 604/96; 604/101
[58] Field of Search ................................ 604/96–104; 606/192, 191

[56] References Cited

U.S. PATENT DOCUMENTS

| | | | |
|---|---|---|---|
| 3,657,744 | 4/1972 | Ersek | 3/1 |
| 4,577,631 | 3/1986 | Kreamer | 128/334 |
| 4,733,665 | 3/1988 | Palmaz | 128/343 |
| 4,856,516 | 8/1989 | Hillstead | 604/104 |
| 4,903,496 | 6/1990 | Bosley, Jr. | 604/101 |
| 4,932,956 | 6/1990 | Reddy et al. | 606/192 |
| 5,024,658 | 6/1991 | Kozlov et al. | 604/96 |

FOREIGN PATENT DOCUMENTS

0277369 12/1987 European Pat. Off. .
3205942 2/1982 Fed. Rep. of Germany .
WO90/15582 6/1990 PCT Int'l Appl. .

*Primary Examiner*—C. Fred Rosenbaum
*Assistant Examiner*—Manuel Mendez
*Attorney, Agent, or Firm*—Ben D. Tobor

[57] ABSTRACT

A balloon device for implanting an aorta or aortodiiliac intraluminal prosthesis for repairing aneurysms utilizes a catheter having two inflatable balloons for expanding two stents associated with the prosthesis.

15 Claims, 1 Drawing Sheet

BALLOON DEVICE FOR IMPLANTING AN AORTIC INTRALUMINAL PROSTHESIS FOR REPAIRING ANEURYSMS

BACKGROUND OF THE INVENTION

1. Field of the Invention

The present invention relates to a balloon device for implanting an aortic or aortodiiliac intraluminal prosthesis for repairing aneurysms, more precisely an arrangement of inflatable balloons which are arranged upon a catheter in order to adapt the means of attachment of a tubular prosthesis to the walls of the aorta.

2. Description of the Prior Art

Intravascular devices, called "stents," which are placed in the organism by means of introducers on balloon catheters, are known.

These stents, used as a means of attachment for intravascular prostheses, are deformed by increasing their diameter when subjected to expansion from inside by inflation of a balloon, until they are imprisoned against the internal side of the arterial wall.

U.S. Pat. application Ser. No. 535,745 of Jun. 11, 1990, in the names of Julio C. Palmaz and the present inventors relates to a prosthesis consisting of two attachment means, or stents, connected by means of a flexible coaxial tube, which is implanted along the arterial zone affected by the aneurysm.

With the current balloon devices, the attachment of stents on ends of a prosthesis is a tedious and time-consuming maneuver.

A device designed for attachment of stents also exists, described in U.S. Pat. No. 3,657,744, issued Apr. 25, 1972 to Robert Ersek, which is not introducible by means of a catheter, and requires additional incisions in the zone to be repaired.

The technique of the introduction of catheters with inflatable balloons is known in valvuloplasty and angioplasty treatments, in which dilation catheters for one or more lumina are used.

If it is desired to implant with the current dilation catheters, the above mentioned prosthesis, consisting of two attachment means or stents, coaxially connected together by means of a flexible tube, it is necessary to use two catheters, one at a time, to consecutively dilate the proximal stent and the distal stent.

This maneuver is difficult and time-consuming, which is not recommendable.

SUMMARY OF THE INVENTION

The device of the present invention simplifies the maneuver by using two balloons upon the same catheter with three lumina for implanting the above mentioned prostheses in the treatment of aneurysms.

The device of the invention also solves the problem arising from implanting the prosthesis when the aneurysm is located in the abdominal aorta very close to the bifurcation of the iliac arteries.

The main object of the invention is a balloon device for implanting an aortic or aortodiiliac intraluminal prosthesis for repairing aneurysms, whose novelty consists in the fact that two inflatable balloons separated by a predetermined distance are located upon a catheter with at least three passages in its interior, each balloon connected to one of said internal passages.

In a preferred mode of execution of the invention with said balloons, the distal balloon is located close to the introduction end of said catheter, and the proximal balloon is located at a distance from the other which is proportional to the length of the prosthesis to be implanted.

In this preferred mode of execution, the proximal balloon has the inlet of the catheter (on the side opposite to that of the distal balloon) displaced from the axis of symmetry of the balloon and at an angle of about 30 degrees in relation to said axis of symmetry.

Both the main object and the advantages of the device of the invention can be evaluated from the following description of the preferred mode of execution of the invention, with reference to the drawings.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

Figure 1:
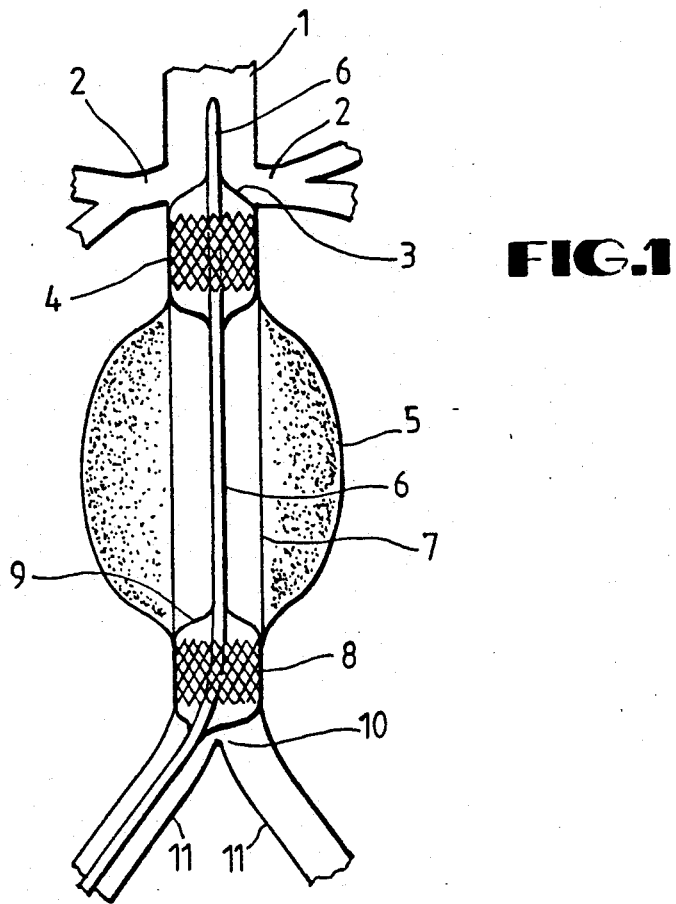
FIG. 1 is a drawing showing the prosthesis at the moment of its implantation.

FIG. 1 shows a design of a portion of the abdominal aorta artery to be treated connected in its upper part with thoracic aorta 1, from which renal arteries 2 depart.

The abdominal aorta presents aneurysm 5, which goes from almost thoracic aorta 1 until bifurcation 10 of iliac arteries 11.

The treatment consists in implanting a prosthesis within the aneurysm 5, consisting of distal stent 4 sutured at one end to flexible liner 7 made of an inert material, such as dacron, and sutured at the other end to another proximal stent 8.

As stated above, the stents 4, 8 are tubes of very fine walls which, when pressure is exerted from the interior of same, dilate to form a tube of walls of greater diameter than the original tube diameter.

The increase in diameter of the stents 4, 8 is attained by means of balloons 3 and 9, which are introduced into the artery by means of catheter 6, which has lines or "lumina" in its interior, through which the fluid insufflated into the balloons 3, 9 passes.

An introducer and guide wire are used for placement of the unit, consisting of a metal wire which is made to pass through an incision in the femoral artery, monitoring the location of same by radioscopy.

After placing the introducer in the area of the aneurysm 5 to be treated, the catheter 6 is introduced, passing one of the lines by the introducer, the stents 4, 8 being previously mounted upon the balloons 3, 9 and compressed to the maximum to make their diameter smaller.

The tube, or liner 7, of inert material is between the two stents 4, 8 which are upon the balloons 3, 9.

When the distal stent 4 with its corresponding balloon 3 in its interior reaches the healthy wall located above the aneurysm 5, the introducer is withdrawn, and the balloon 3 is inflated up to its maximum diameter, as a result of which stent 4 takes the form indicated in FIG. 1, being implanted against the wall of the artery.

The procedure is the same with stent 8 and proximal balloon 9.

The inflation of balloons 6 and 9 can be done either simultaneously or alternately.

After the stents 4, 8 have been put into place, the balloons 3, 9 are deflated, and the catheter is withdrawn with same.

When the lower part of the aneurysm 5 is located close to bifurcation 10 of iliac arteries 11, as shown in FIG. 1, the correct attachment of proximal stent 8 becomes difficult, because in this place catheter 6 is not coaxial with the abdominal aorta, the pressure exerted by balloon 9 against the interior wall of the stent 8 being unequal.

Figure 2:
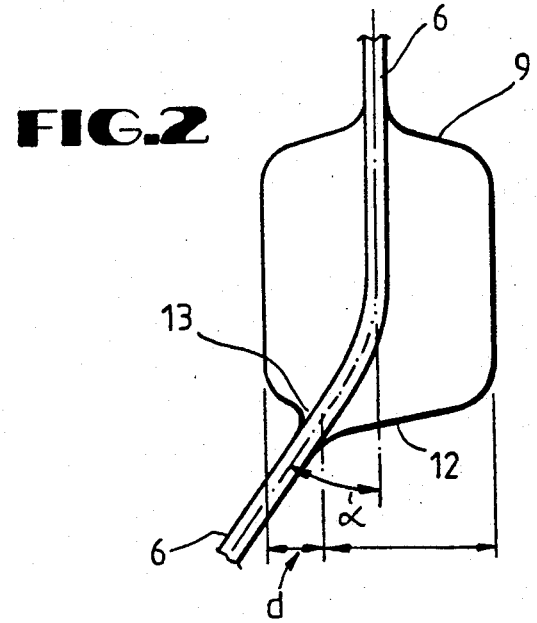
FIG. 2 is a drawing of the form of the proximal balloon of the device of the invention.

In this case, proximal balloon 9 should take the special form indicated in FIG. 2.

Proximal balloon 9 has outlet 13 of catheter 6 located at distance "d" from the balloon 9 longitudinal axis, which is approximately half the radius of balloon 9, and catheter 6 leaves balloon 9 at angle alpha of approximately 30 degrees in relation to the longitudinal axis of balloon 9.

The interior part of balloon 9 takes approximately saddle form 12, because same is located at bifurcation 10 of the iliac arteries.

When the aneurysm 5 involves iliac arteries 11, liner 7 of bifurcated tube form should be used, in which case proximal balloon 9 should have a diameter corresponding to that of iliac artery 11, and it should be coaxial to catheter 6 as well as distal balloon 3.

In the preferred form of execution of the device, catheter 6 has a length of between 50 and 75 cm, with thickness of between 5 and 10 of the French scale, and it is made of polyvinyl chloride, for example, its distal end having a truncated conical point with blunt edges.

The central passage or central lumen of the catheter 6 will be used for introduction of the guide cord and also for injection of contrast substance. The other two passages, or lumina, will be used for the inflation and deflation of each of the balloons 3, 9.

In its turn, the catheter 6 will have surface marks every 15 cm and radiopaque marks at the beginning and end of each balloon 3,9.

In the preferred form of execution, the balloons 3, 9 are made of polyvinyl chloride or polyethylene and are of cylindrical form with blunt edges, with a length of between 3 and 5 cm along the catheter 6 and a diameter of between 16 and 30 mm.

It is to be understood that the invention is not limited to the exact details of construction, operation, exact materials or embodiment shown and described, as obvious modifications and equivalents will be apparent to one skilled in the are. Accordingly, the invention is therefore to be limited only by the scope of the appended claims.

We claim:

1. A balloon device for implanting an intraluminal aortic or aortodiiliac prosthesis for repairing aneurysms, comprising:
   a catheter having a longitudinal axis and at least three internal passages;
   first and second inflatable balloons disposed upon the catheter and separated by a predetermined distance, each balloon connected to at least one of the internal passages the second balloon having first and second ends and a longitudinal axis which is substantially parallel to the longitudinal axis of the catheter, the first end of the second balloon being disposed closer to the first balloon than the second end of the second balloon; and
   the second end of the second balloon having an outlet for the catheter, the outlet being displaced from the longitudinal axis of the second balloon at an angle of approximately thirty degrees.

2. The balloon device of claim 1, wherein the catheter has an introduction end and the first balloon is located proximate the introduction end of the catheter and the second balloon is located at a distance from the first balloon which is proportional to the length of the prosthesis to be implanted.

3. The balloon device of claim 1, wherein the second balloon has a substantially tubular cross-sectional configuration with a radial dimension R; and the catheter enters the second end of the second balloon at an approximate distance of $\frac{1}{2}R$ from the longitudinal axis of the second balloon.

4. The balloon device of claim 2, wherein the first and second balloons each have a substantially tubular cross-sectional configuration with a radial dimension R about their longitudinal axes; the radial dimension R of the first balloon being greater than the radial dimension R of the second balloon, and the catheter passes through the first and second balloons coaxially with the longitudinal axes of the first and second balloons.

5. A method for implanting an intraluminal aortic or aortodiiliac prosthesis for repairing aneurysms, the prosthesis having first and second ends with a tubular liner disposed therebetween, and first and second stents attached to the liner at each of its ends comprising the steps of:
   disposing upon a catheter, having a longitudinal axis, first and second inflatable balloons separated by a predetermined distance, each balloon having first and second ends, the first end of the second balloon being disposed closer to the first balloon than the second end of the second balloon, the second balloon having a longitudinal axis which is substantially parallel to the longitudinal axis of the catheter;
   disposing the catheter to enter the second end of the second balloon at an angle of approximately thirty degrees with respect to the longitudinal axis of the second balloon;
   mounting the prosthesis upon the catheter;
   disposing the first and second stents respectively upon the first and second balloons;
   introducing the catheter, having the prosthesis disposed thereon, into the aneurysm by catheterization;
   inflating the first and second balloons to implant the prosthesis within the aneurysm; and
   deflating the first and second balloons and removing the catheter from the aneurysm.

6. The method of claim 5, including the step of inflating the first balloon to implant the first stent; and after inflating the first balloon, inflating the second balloon to implant the second stent.

7. The method of claim 5, including the step of simultaneously inflating the first and second balloons.

8. The method of claim 7, including the step of disposing the first and second balloons coaxially with the longitudinal axis of the catheter.

9. The method of claim 7, including the step of:
   utilizing a catheter having three passages extending through the catheter, with one passage associated with each of the first and second balloons.

10. A balloon device for implanting an intraluminal aortic or aortodiiliac prosthesis for repairing aneurysms, comprising:
- a catheter having a longitudinal axis and at least three internal passages;
- first and second inflatable balloons disposed upon the catheter and separated by a predetermined distance, each balloon connected to at least one of the internal passages, wherein the second balloon has a substantially tubular cross-sectional configuration with a radial dimension R, first and second ends, and a longitudinal axis which is substantially parallel to the longitudinal axis of the catheter, the first end of the second balloon being disposed closer to the first balloon than the second end of the second balloon; and
- the second end of the second balloon having an outlet for the catheter, the outlet being displaced from the longitudinal axis of the second balloon at an approximate distance of $\frac{1}{2}R$.

11. The balloon device of claim 10; wherein, the catheter has an introduction end and the first balloon is located proximate the introduction end of the catheter and the second balloon is located at a distance from the first balloon which is proportional to the length of the prosthesis to be implanted.

12. The balloon device of claim 10, wherein the first and second balloons each have a substantially tubular cross-sectional configuration with a radial dimension R; and the radial dimension R of the first balloon is greater than the radial dimension R of the second balloon.

13. A method for implanting an intraluminal aortic or aortodiiliac prosthesis for repairing aneurysms, the prosthesis having first and second ends with a tubular liner disposed therebetween, and first and second stents attached to the liner at each of its ends, comprising the steps of:
- disposing upon a catheter having a longitudinal axis, first and second inflatable balloons separated by a predetermined distance, each balloon having first and second ends, the first end of the second balloon being disposed closer to the first balloon than the second end of the second balloon, the second balloon having a substantially tubular cross-sectional configuration about the longitudinal axis of the catheter;
- disposing the catheter to enter the second end of the second balloon at a distance from the longitudinal axis of the second balloon of approximately $\frac{1}{2}$ of the radial dimension of the second balloon;
- mounting the prosthesis upon the catheter;
- disposing the first and second stents respectively upon the first and second balloons;
- introducing the catheter, having the prosthesis disposed thereon, into the aneurysm by catheterization;
- inflating the first and second balloons to implant the prosthesis within the aneurysm; and
- deflating the first and second balloons and removing the catheter from the aneurysm.

14. The method of claim 13, including the step of simultaneously inflating the first and second balloons.

15. The method of claim 13, including the step of inflating the first balloon to implant the first stent; and after inflating the first balloon, inflating the second balloon to implant the second stent.

* * * * *

UNITED STATES PATENT AND TRADEMARK OFFICE
CERTIFICATE OF CORRECTION

PATENT NO. : 5,219,355
DATED : June 15, 1993
INVENTOR(S) : Juan C. Parodi, et. al.

It is certified that error appears in the above-indentified patent and that said Letters Patent is hereby corrected as shown below:

Title page, item [57], Abstract, col. 2, line 1, delete "aortodiiliac" and insert --aortobiiliac--.
Column 1, line 9, delete "aortodiiliac" and insert --aortoviiliac--.
    line 60, delete "aortodiiliac" and insert --aortoviiliac--.
Column 3, line 58, delete "aortodiiliac" and insert --aortobiiliac--.
Column 4, line 28, delete "aortodiiliac" and insert --aortobiiliac--.
Column 5, line 2, delete "aortodiiliac" and insert --aortobiiliac--.
    line 33, delete "aortodiiliac" and insert --aortobiiliac--.

Signed and Sealed this

Twelfth Day of September, 1995

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,219,355
DATED      : June 15, 1993
INVENTOR(S) : Juan C. Parodi, et. al.

It is certified that error appears in the above-identified patent and that said Letters Patent is hereby corrected as shown below:

Title page, item (57), Abstract, col. 2, line 1, delete "aortodiiliac" and insert--aortobiiliac--.

Column 1, line 9, delete "aortodiiliac" and insert--aortobiiliac--.
          line 60, delete "aortodiiliac" and insert--aortobiiliac--.
Column 3, line 58, delete "aortodiiliac" and insert--aortobiiliac--.
Column 4, line 28, delete "aortodiiliac" and insert--aortobiiliac--.
Column 5, line 2, delete "aortodiiliac" and insert--aortobiiliac--.
          line 33, delete "aortodiiliac" and insert--aortobiiliac--.

This certificate supersedes Certificate of Correction issued September 12, 1995.

Signed and Sealed this

Twenty-second Day of December, 1998

Attest:

Attesting Officer

BRUCE LEHMAN

Commissioner of Patents and Trademarks